(12) United States Patent
Shi

(10) Patent No.: US 7,175,643 B2
(45) Date of Patent: Feb. 13, 2007

(54) AUTOMATIC SAFE SELF-DESTRUCTIVE DISPOSABLE BLOOD SAMPLING DEVICE

(76) Inventor: Guoping Shi, No. 32, Xinlian Road, Pingjiang District, Suzhou City, Jiangsu Province (CN) 215008

( * ) Notice: Subject to any disclaimer, the term of this patent is extended or adjusted under 35 U.S.C. 154(b) by 497 days.

(21) Appl. No.: 10/644,652

(22) Filed: Aug. 20, 2003

(65) Prior Publication Data

US 2006/0058828 A1    Mar. 16, 2006

(30) Foreign Application Priority Data

May 12, 2003    (CN) .................................. 03221812

(51) Int. Cl.
*A61B 17/32*    (2006.01)
*A61B 17/14*    (2006.01)
*A61B 5/00*    (2006.01)

(52) U.S. Cl. ........................ 606/181; 606/167; 600/583
(58) Field of Classification Search ........ 606/181–185, 606/167; 604/136, 137; 600/583
See application file for complete search history.

(56) References Cited

U.S. PATENT DOCUMENTS

| | | | |
|---|---|---|---|
| 4,099,520 A | 7/1978 | Decker et al. | |
| 5,100,427 A * | 3/1992 | Crossman et al. | 606/182 |
| 5,133,730 A * | 7/1992 | Biro et al. | 606/182 |
| 5,304,193 A * | 4/1994 | Zhadanov | 606/182 |
| 5,873,887 A | 2/1999 | King et al. | |
| 6,514,270 B1 * | 2/2003 | Schraga | 606/182 |
| 6,719,771 B1 * | 4/2004 | Crossman | 606/182 |

\* cited by examiner

*Primary Examiner*—Glenn K. Dawson
*Assistant Examiner*—Kathleen Sonnett
(74) *Attorney, Agent, or Firm*—Hamilton, Brook, Smith & Reynolds, P.C.

(57) ABSTRACT

A one time use disposable blood sampling device comprises a case defining a shoot chamber with a lancet-exiting hole, and a lancet disposed slidably in the shoot chamber with a puncturing tip pointed to the lancet-exiting hole. The sampling device further comprises a locking and shooting structure formed of an elastic arm button and an elastic arm. The button engaging end of the elastic arm button faces a locking hole on a side wall of the case. A free end of the elastic arm engages with the locking hole in a locking state. Upon pressing of the elastic arm button, the elastic arm disengages from the locking hole, and the lancet moves under spring action inside the shoot chamber causing the elastic arm to contact a bevel. A root portion of the elastic arm is notched or has a shrink neck which causes the elastic arm to automatically self-break upon contact with the bevel.

11 Claims, 3 Drawing Sheets

AUTOMATIC SAFE SELF-DESTRUCTIVE DISPOSABLE BLOOD SAMPLING DEVICE

RELATED APPLICATION

This application claims priority under 35U.S.C. § 119 or 365 to Chinese Application No. 03221812.5, filed May 12, 2003, The entire teachings of the above application are incorporated herein by reference.

TECHNICAL FIELD OF THE INVENTION

The present invention relates to an automatic safe disposable blood sampling device for medical use, more particularly, to an automatic safe blood sampling device which employs a self-destructive locking and shooting structure to perform one-off shoot, the locking and shooting structure of the blood sampling device is self-destructed in use and can not be reused.

BACKGROUND OF THE INVENTION

Various types of medical blood sampling device are known, but there is a tendency to develop a "mini" blood sampling device which is safe and disposable simple in structure, low in cost, convenient to operate, and so on. Presently, most mini blood sampling devices available in the market have simple structures, and are disposable and convenient to operate, however, the structures of these blood sampling devices themselves can be reused, strictly speaking, such designs are not safe. In order to overcome the above defects and to eradicate the potential safety hazard, there is proposed a Chinese Utility Model No. 02221043.1 published on Apr. 2, 2003 and entitled "automatic safe destructive blood sampling device". During use, a locking and shooting structure of the Chinese Utility Model No. 02221043.1 disengages an elastic wedge and breaks the elastic wedge from the root portion which has a notch, using a side component of force generated by contact between a bevel surface of a block and the elastic wedge, thus achieving one-off shooting and being beyond retrieval. Therefore, the locking and shooting structure of this blood sampling device is disposable and eliminates possibility of reuse, thus being worthy of disposable product.

The present invention provides another automatic safe disposable blood sampling device having a self-destructive locking and shooting structure according to the above principle of "one-off shooting and being not reused", that is, the locking and shooting structure is self-destructed after shooting and can not be reused.

SUMMARY OF INVENTION

In order to accomplish the above object, there is provided an automatic safe self-destructive disposable blood sampling device, comprising a case; a lancet and a spring, the case defines a shoot chamber provided with a lancet-exiting hole at a front end thereof, the lancet is provided with a puncturing tip on a front portion thereof, the puncturing tip points to the lancet-exiting hole in an alignment manner, the spring is disposed at back of the lancet in the shooting direction, a locking and shooting structure is provided on a side of the lancet and the case along a compression path of the spring, the locking and shooting structure is composed of an elastic arm button on the case and an elastic arm on the lancet, the elastic arm button is an extended structure on the side of the case, its button function end faces a locking hole provided on a side wall of the case, the elastic arm is another extended structure on a side of lancet corresponding to the side wall of the case, its free end is engagable with the locking hole in a locking state, and its root portion is provided with a notch or a shrink neck on which stress is easily concentrated.

The related contents and variations of the above technical scheme are explained as follows:

1. In the above scheme, the "lancet" is a member having a lancet body and generally composed of the lancet body and a member wrapping the lancet body. In order to protect the puncturing tip, a lancet cap can be provided at front of the lancet body, one end of the lancet cap is exposed outside of the lancet-exiting hole and the other end thereof passes through the lancet-exiting hole and sheathes the puncturing tip.

2. In the above scheme, the locking and shooting structure is generally provided on a side of the blood sampling device, the side of the blood sampling device alternates sliding guide structures on both side thereof, that is, if sliding guide grooves and guide ribs are provided on two sides of the blood sampling device, the locking and shooting structure is provided on a side of the blood sampling device which is different from the above-said two sides, for example, the locking and shooting structure is provided on an upper side of the blood sampling device in FIG. 1.

3. In the above technical scheme, the "shrink neck" indicates that the elastic arm is self-destructive in use by employing a structure whose section shrinks. In fact, this structure is an equivalent to a notch.

4. In the above technical scheme, the notch can be provided on either inner side or outer side of the elastic arm, but it is preferable that the notch is provided on the outer side, so that the stress concentration is easily generated.

5. In the above technical scheme in order to ensure that the elastic arm is easy to be broken and self-destructed when the elastic arm button is pressed downwardly in the drawings, it is preferable that the notch on which the stress is concentrated has a V-shape.

6. In the above technical scheme, in order to ensure that the elastic arm is self-destructed when it is bent, an avoiding space is provided in a direction on which the elastic arm is bent inwardly.

7. In the above technical scheme, in order to ensure a secure locking engagement between a free end of the elastic arm and the inner side surface of the locking hole, a special catching groove can be provided on a free end of the elastic arm and the lancet can be kept in a securely locking state through the catching groove.

The operation of the present invention is described as follows:

Before using the blood sampling device, the spring is kept in a compressed state, the inner side surface of the locking hole is caught by the catching groove on the free end of the elastic arm on the lancet, so that the lancet is in a state to be ejected, as shown in FIG. 1. When a user presses downwardly the elastic arm button with his finger, the button urges the elastic arm inwardly so as to disengage the catching groove from the locking hole, the spring pushes the lancet along a sliding guide structure to eject out, as shown in FIG. 2. Since a notch is provided in the root portion, the elastic arm is broken to be self-destructed due to stress concentration on the notch when it is bent inwardly, so that the lancet can not return to its original ejectable state, as shown in FIG. 3.

The present invention has the following advantageous technical effects by comparison with the prior art.

1. There is provided a notch or a shrink neck on which stress is easy to concentrate, so that the elastic arm is broken to self-destruct while it is pressed by the button to disengage from the locking hole, thus achieving the effects of one-off shooting and the blood sampling device being beyond retrieve. The technical scheme of the present invention has a simple and skillful structure and is non-obvious over the prior art, thus embodying novelty and inventiveness of the present invention.

2. The present invention is easy to use, that is, when operating, the blood sampling device is firstly pointed to a blood sampling position in alignment, and the button is then pressed, thus accomplishing blood sampling. If the lancet cap is provided, the lancet cap is firstly rotated and drawn off, then the above operation is performed.

3. The puncturing tip can be retraced into the case after sampling blood and not be exposed outside, thus ensuring the safety of the blood sampling device after use.

4. The present invention not only has small size and volume, good manufacturability, low cost and high acceptability but also is light, thus being a compact automatic safe disposable "mini" blood sampling device.

BRIEF DESCRIPTION OF THE DRAWINGS OF THE INVENTION

Figure 1:
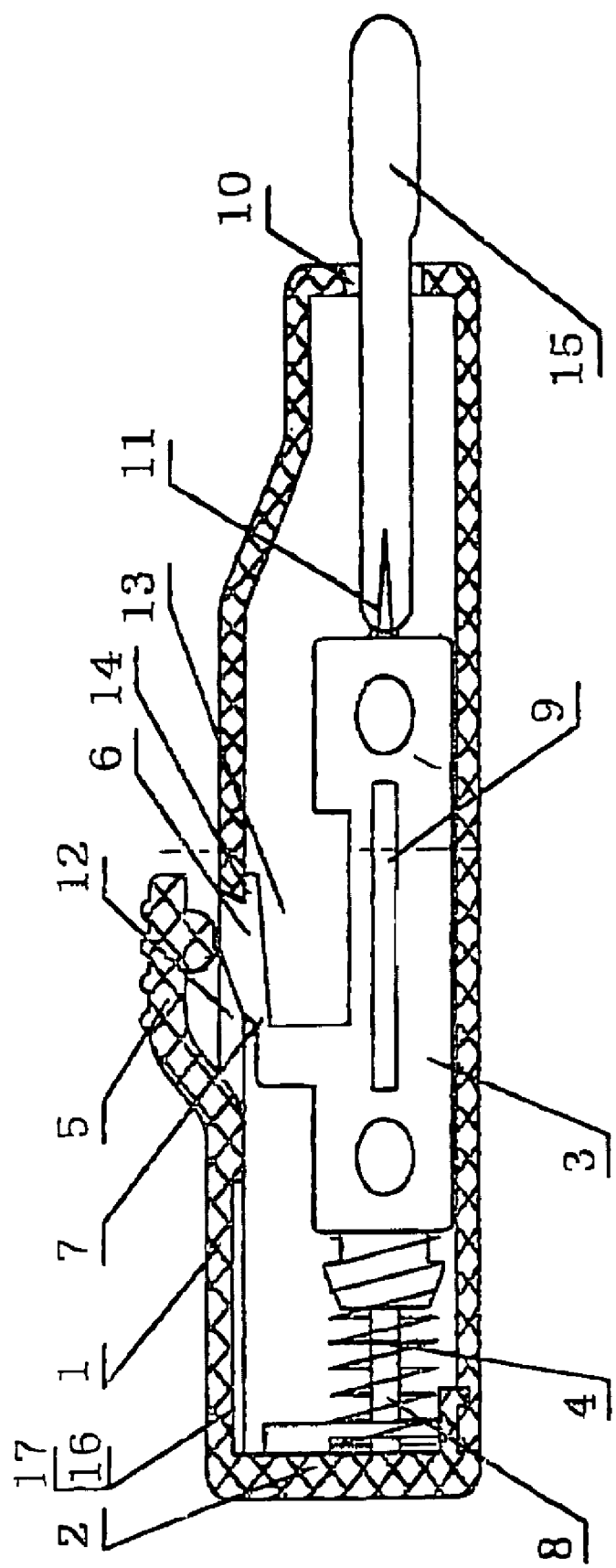
FIG. 1 is a structural sectional view of the present invention showing an assembled structure before use.

In the above drawings, the reference numerals denote the following members respectively: 1. case; 2. end cover; 3. lancet; 4. spring; 5. elastic arm button; 6. elastic arm; 7. notch; 8. guide groove; 9. guide rib; 10. lancet-exiting hole; 11. puncturing tip; 12. locking hole; 13 avoiding space; 14. catching groove; 15. lancet cap; 16. projection rib; 17. recess.

DETAILED DESCRIPTION OF THE EMBODIMENTS OF THE INVENTION

Embodiments of the present invention will be described in detail with reference to the accompanying drawings.

Figure 2:
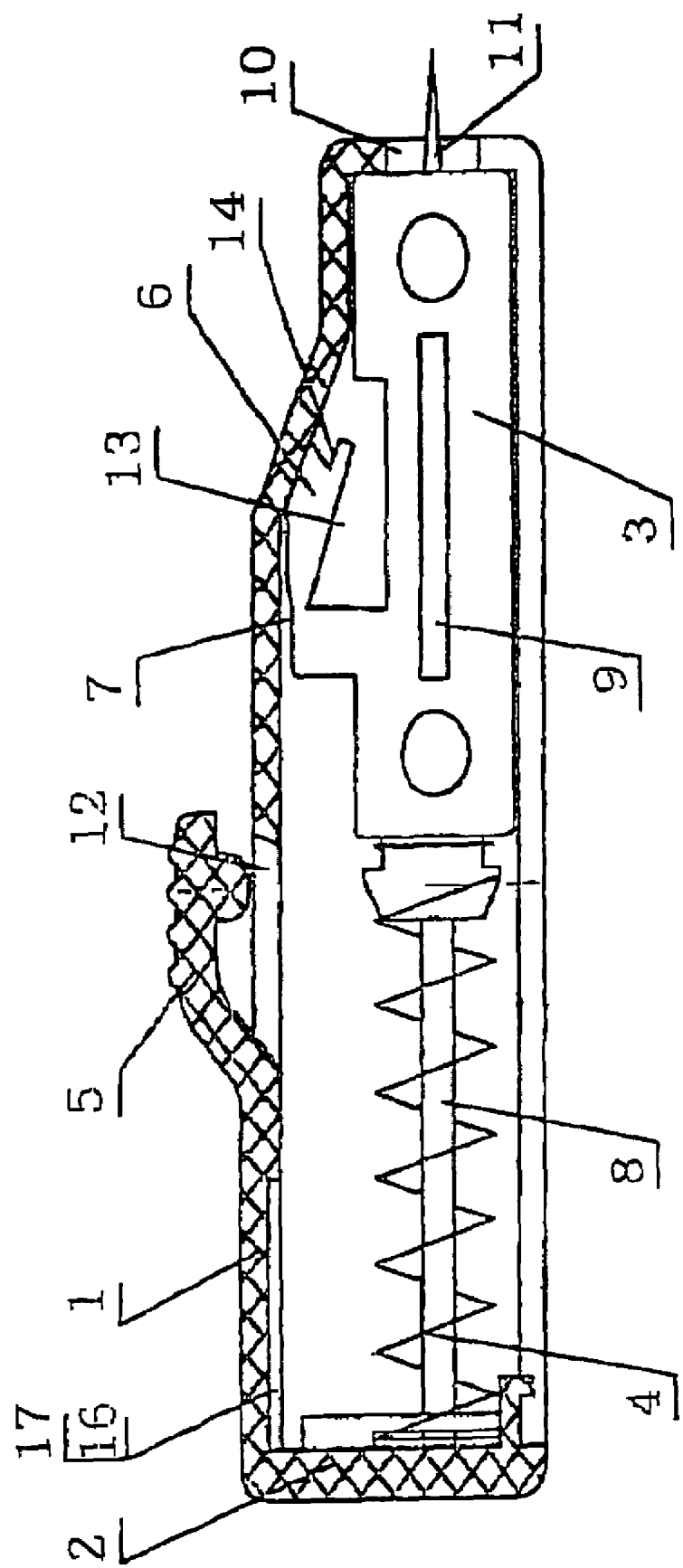
FIG. 2 is a structural sectional view of the present invention showing an assembled structure in use to take blood.
Figure 3:
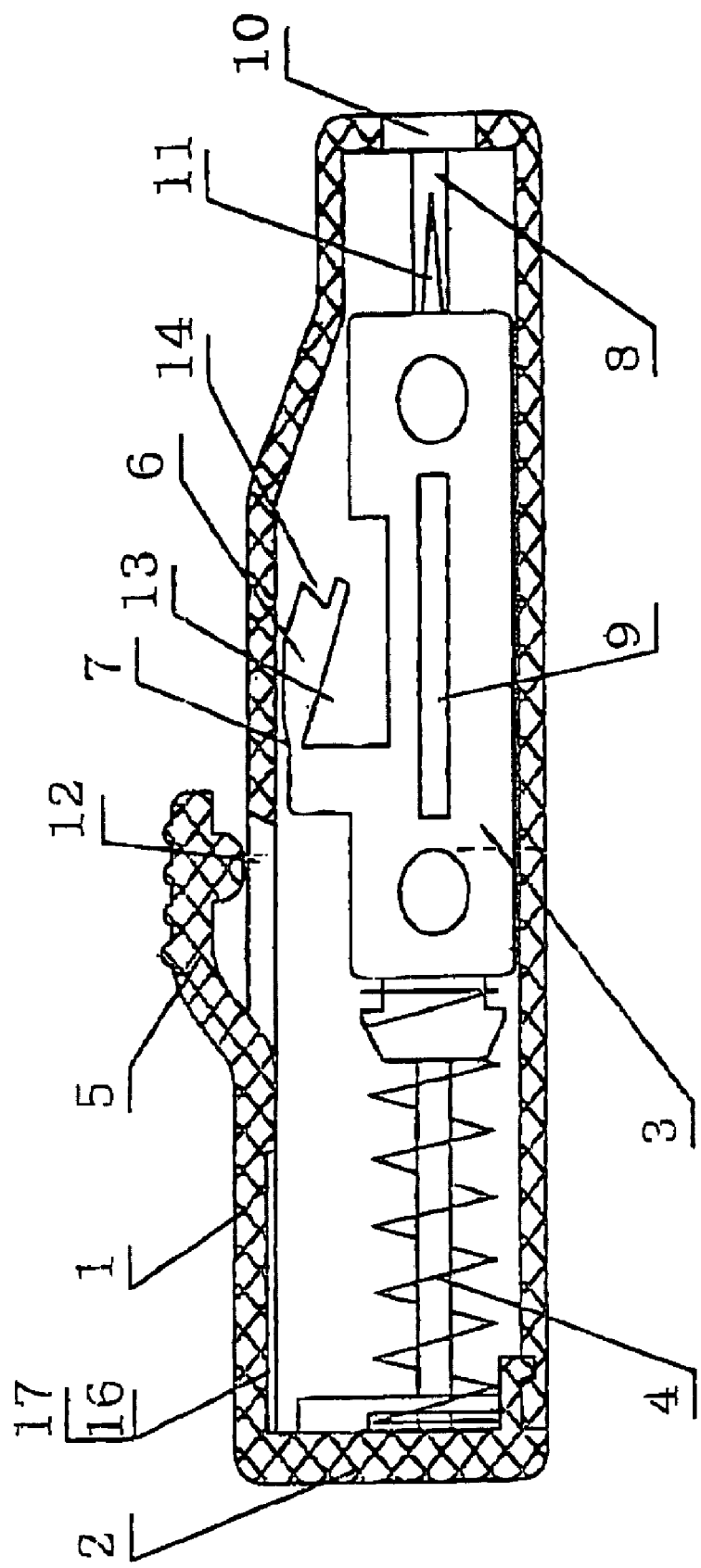
FIG. 3 is a structural sectional view of the present invention showing an assembled structure after use.

As shown in FIG. 1 to FIG. 3, there is provided an automatic safe disposable blood sampling device, comprising a case 1, an end cover 2, a lancet 3 and a spring 4. The end cover 2 covers a tail end of the case 1, a lower side of the end cover 2 connects to the case 1 by a hook, and a projection rib 16 on an upper side thereof is inserted into a recess 17 in the case 1, so that the end cover 2 can be guided advantageously before it is pressed tightly against the tail end of the case 1. The case 1 and the end cover 2 form a housing for the blood sampling device, the housing defines an shoot chamber having a lancet-exiting hole 10 at the front end thereof. The lancet 3 is disposed in the shoot chamber. As shown in FIG. 3, the lancet 3 is provided with guide ribs 9 at an outer side and an inner side thereof respectively, the guide ribs 9 engage corresponding guide grooves 8 provided on sides of the shoot chamber respectively so as to form an shoot guide structure. The lancet 3 comprises a lancet body and a plastic member warping the lancet body, the lancet 3 has a puncturing tip 11 at the front portion thereof, the puncturing tip 11 points to the lancet-exiting hole 10 in an alignment manner, a lancet cap 15 sheathes the puncturing tip 11, a head portion of the lancet cap 15 is exposed outside of the lancet-exiting hole 10. The spring 4 is disposed at back of the lancet 3 in an shoot direction, one end of the spring 4 is fixed to a tail end of the lancet 3, and the other end thereof is fixed to the end cover 2. A locking and shooting structure is provided at the upper side of the lancet 3 and the case 1 along the compression path of the spring 4, the locking and shooting structure is composed of an elastic arm button 5 on the case 1 and an elastic arm 6 on the lancet 3. The elastic arm button 5 is an extended structure at the upper side of the case 1, its button engaging portion faces a locking hole 12 provided on a side wall of the case 1. The elastic arm 6 is an extended structure at the upper side of the lancet 3 and provided with a catching groove 14 at a free end thereof, the catching groove 14 employs bevel surfaces and engages the side walls of the locking hole 12 in a locking state, so that the lancet 3 and the spring 4 is in a compressed state to be ejected. An indention 7 on which stress is easy to concentrate is provided on the root portion of the elastic arm 6, the indention 7 has a V-shaped notch and is provided on the outside of the elastic arm 6. A sufficient avoiding space 13 is provided in a direction on which the elastic arm 6 is bent inwardly. When the elastic arm button 5 is pressed downwardly, the elastic am 6 is bent inwardly towards the lancet 3, during the bending of the elastic arm 6, the catching groove 14 is disengaged from the locking hole 12 so that the lancet 3 turns into a shooting state, on the other hand, stress is concentrated on the indention 7 so that the elastic arm 6 is broken to be self-destructed, therefore, the blood sampling device falls out of use automatically after one-off shoot.

While the invention has been shown and described with reference to certain embodiments thereof, it will be understood by those skilled in the art that various changes in form and details may be made therein without departing from the spirit and scope of the invention as defined by the appended claims.

What is claimed is:

1. An automatic safe disposable blood sampling device, comprising:

a case defining a shoot chamber, said shoot chamber being provided with a lancet-exiting hole at a front end thereof;

a lancet disposed slidably in said shoot chamber and provided with a puncturing tip at a front portion thereof, said puncturing tip being pointed to said lancet-exiting hole in an alignment manner;

a spring disposed at back of said lancet in a shooting direction of said lancet; and a locking and shooting structure provided on a side of said lancet and said case along a compression path of said spring, said locking and shooting structure comprising:

an elastic arm button being an extended structure on a side of said case;

a button engaging end of said elastic arm button facing a locking hole provided on a side wall of said case, the side wall having a bevel;

an elastic arm being an extended structure on a side of said lancet corresponding to said side wall of said case;

a free end of said elastic arm being engagable with said locking hole in a locking state, the free end employing the bevel; and a root portion of said elastic arm being provided with a notch or a shrink neck on which stress is easily concentratable, said notch or shrink neck forming a self-destructive breaking point of said elastic arm, such that the elastic arm is automatically self broken by contacting the bevel and boarding inwardly when said lancet changes from the locking state to a shooting state.

2. The blood sampling device according to the claim 1, wherein said notch is provided on an outer side of said elastic arm.

3. The blood sampling device according to the claim 1, wherein said notch on which stress in easy to concentrate has a V-shaped notch.

4. The blood sampling device according to the claim 1, wherein an avoiding space is provided in a direction on which said elastic arm is bent inwardly.

5. The blood sampling device according to the claim 1, wherein said free end of said elastic arm is provided with a catching groove to be engaged with an inner side surface of said locking hole.

6. A method for sampling blood for penetrating skin to sample blood therefrom, comprising the steps of:
  a) providing an automatic blood sampling device, the sampling device comprising:
    a case defining a shoot chamber, said shoot chamber being provided with a lancet-exiting hole at a front end thereof;
    a lancet disposed slidably in said shoot chamber and provided with a puncturing tip at a front portion thereof, said puncturing tip being pointed to said lancet-exiting hole in an alignment manner;
    a spring disposed at back of said lancet in a shooting direction of said lancet; and
    a locking and shooting structure provided on a side of said lancet and said case along a compression path of said spring, said locking and shooting structure comprising:
      an elastic arm button being an extended structure on a side of said case;
      a button engaging end of said elastic arm button facing a locking hole provided on a side wall of said case; the side wall having a bevel;
      an elastic arm being an extended structure on a side of said lancet corresponding to said side wall of said case;
      a free end of said elastic arm being engagable with said locking hole in a locking state the free end employing the bevel; and
      a root portion of said elastic arm being provided with a notch or a shrink neck on which stress is easily concentratable, said notch or shrink neck forming a self-destructive breaking point of said elastic arm, such that the elastic arm is automatically self broken by contacting the bevel and boarding inwardly when said lancet changes from the locking state to a shooting state;
  b) applying the front end against a target area of a subject; and
  c) actuating the elastic arm button to make a contact with the elastic arm, thereby moving said lancet and puncturing the target area.

7. The method according to claim 6, wherein said notch is provided on an outer side of said elastic arm.

8. The method according to claim 6, wherein said notch on which stress in easy to concentrate has a V-shaped notch.

9. The method according to claim 6, wherein an avoiding space is provided in a direction on which said elastic arm is bent inwardly.

10. The method according to claim 6, wherein said free end of said elastic arm is provided with a catching groove to be engaged with an inner side surface of said locking hole.

11. The method of according to claim 6 further including the step of breaking said elastic arm upon the actuation.

\* \* \* \* \*